United States Patent [19]

Kerschgens

[11] Patent Number: 4,560,883

[45] Date of Patent: Dec. 24, 1985

[54] METHOD OF AND DEVICE FOR ULTRAVIOLET IRRADIATION

[76] Inventor: Johann J. Kerschgens, Arabellastrasse 5/1815, D-8000 Muenchen 81, Fed. Rep. of Germany

[21] Appl. No.: 480,662

[22] Filed: Mar. 31, 1983

[30] Foreign Application Priority Data

Sep. 1, 1982 [DE] Fed. Rep. of Germany ....... 3232537
Dec. 9, 1982 [DE] Fed. Rep. of Germany ....... 3245655
Dec. 9, 1982 [DE] Fed. Rep. of Germany ....... 3245654

[51] Int. Cl.$^4$ ............................................. G01J 1/00
[52] U.S. Cl. ........................... 250/504 R; 250/504 H; 250/493.1
[58] Field of Search ............... 250/504 R, 504 H, 493, 250/495; 128/395, 396; 313/12, 28

[56] References Cited

U.S. PATENT DOCUMENTS

| | | | |
|---|---|---|---|
| 1,692,413 | 11/1928 | Lewis | 250/495 |
| 3,792,230 | 2/1974 | Ray | 219/343 |
| 3,831,289 | 8/1974 | Knight | 34/4 |
| 4,177,384 | 12/1979 | Wolff | 250/494 |
| 4,298,005 | 11/1981 | Mutzhas | 128/396 |

Primary Examiner—Bruce C. Anderson
Assistant Examiner—Paul A. Guss
Attorney, Agent, or Firm—Michael J. Striker

[57] ABSTRACT

A method is described by means of which a UV radiation beam is modified by passing a stream of a gas around the radiation source. The device for carrying out this method includes a gas duct connectable at its inlet to a source of gas such as a hot-air blower. A UV-radiation source with a reflector is located at the outlet of the duct so as to permit passage of a stream of gas in the direction of the emitted radiation beam and a part of the gas stream is deflected around the source. A baffle plate permeable to radiation is located in front of the radiation source to create an increased dynamic gas pressure.

23 Claims, 13 Drawing Figures

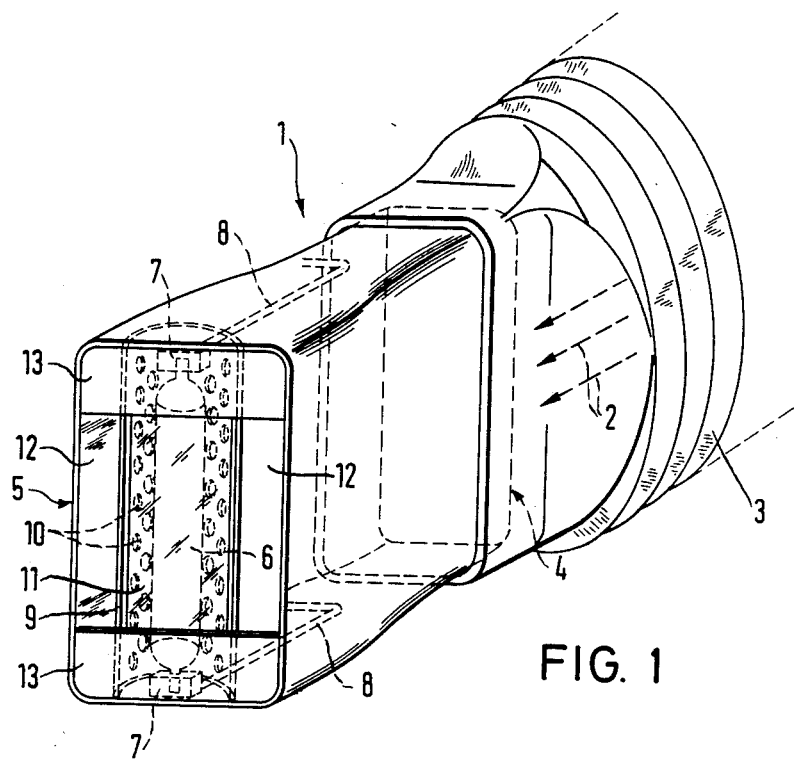
FIG. 1
FIG. 2
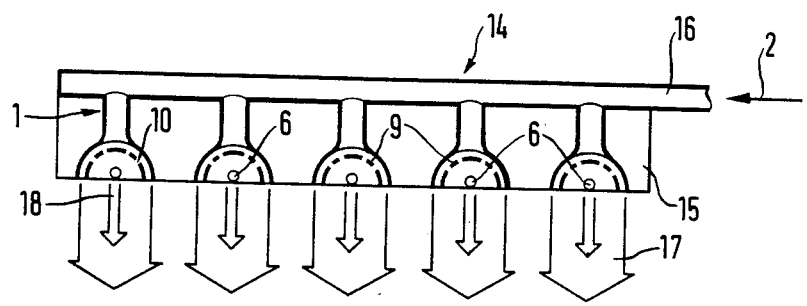

METHOD OF AND DEVICE FOR ULTRAVIOLET IRRADIATION

BACKGROUND OF THE INVENTION

The present invention relates in general to a source of ultraviolet radiation and in particular to a method of and device for changing or adjusting the intensity and effects of ultraviolet radiation.

Ultraviolet radiation, in the following text referred to a UV-radiation, is divided according to its wavelengths into UVA-, UVB- and UVC radiation bands. The UVA band has a wavelength between 315 and 400 nl and its share in the sunlight amounts to about 5%. The UVB radiation band has a wavelength from 280 to 315 nm and in the European geographical latitudes constitutes about 0.04 to 0.12% of sunlight. The UVC radiation band has its wavelengths in the range between 200 and 280 nm which even if emitted by sun, are blocked by the earth's atmosphere.

The effect of UV radiation is manysided. For example, human skin becomes tanned in response to the exposure of UVB- and UVA radiation. The UVC radiation generates ozone in the atmosphere and in addition, destroys microorganisms such as bacteria, viruses, spores, yeast, algaes, protozoa and mold fungi. In the human skin, UVC radiation produces histamin, causing sunburn, and destroys bacteria which interfere with regulation of fatty films. The radiation therapy employs UV radiation for healing purposes, and in photochemistry the UV radiation enhances chemical reactions.

In utilizing UV radiation, different types of radiation sources and irradiation devices have been developed in order to transmit the desired radiation band such as UVA- and/or UVB, or UVC radiation band. The intensity of radiation and the wavelength range generated in such prior-art devices is normally constant. Of course, the intensity can be adjusted by conventional filters or by electrical means, for example, by switching on or off individual radiation sources when the device includes a plurality of light sources transmitting at different wavelengths. This dosing capability for controlling the time of irradiation however is in most cases insufficient especially when it is desired to adjust the exposure or dose to skin conditions of individual patients. For example, the sensitivity of different parts of the human body to radiation is not uniform. While abdomen, breast or back can withstand 75 to 100% of a certain dose of irradiation, the sensitivity of the lower arm or of the surface of the shinbone can tolerate only 25% of this dose. Moreover, the permissible dose depends on age, on hair color, on sex and other constitutional and racial peculiarities as well as on year's season and condition of toners of the vegetative nervous system. At present time, the dosimetry is based on the generation of erythrism, that means it is concerned with the sensitivity of human skin defining a maximum sensitivity at 296.7 nm (finsen). The measure for effectiveness of the radiation relates to a fictitious "average person" so that the individual dose must be ascertained empirically. The same considerations are valid in dosing radiation for photochemical and the like processes in which UV radiation is used.

In known phototherapy apparatuses or solaria, the intensity of radiation (radiation strength in finses) is adjustable by varying the number of active radiations and their mutual arrangement, by adjusting the distance from the plane of radiation, and by varying exposure time. In addition, it is known to employ filters for absorbing certain wavelengths, the effect of which may be harmful. Furthermore, large area solaria have been developed which permit the irradiation of the whole body of a patient, whereby the distribution of intensity of radiation is adjusted to different sensitivities of various parts of the patient's body. This known intensity adjustment is attainable by the application of different filters and/or radiation sources transmitting at different intensities or wavelengths. Such diversified radiation sources are arranged in the radiation plane of the apparatus according to the outlines of the body to be irradiated. This solution however, is suitable for relatively small transmitting distances only, for example when the spacing between the source and the object to be irradiated is smaller than one meter but even in this case the results are not completely satisfactory.

Known also are the so-called "home suns" which denotes radiation sources using mercury vapor lamps as well as electrically heated rods for transmitting infrared (IR) radiation. The ultraviolet rays of mercury vapor lamps are used in irradiating skin in order to achieve therapeutic and cosmetic effects and/or to increase the resistance of the human body. The ultraviolet rays, as known, assist in photobiologic effects in the skin. The home suns emit short-wave UV radiation, particularly UVC radiation which produces initially erythema and after several days in indirect pigmentation or tan of the skin. On the other hand, high doses of longer UV-rays (UVA) lead to a direct pigmentation without the occurrence of erythema. The maximum of skin sensitivity to direct pigmentation is at the wavelength of about 360 nm. The latter tanning process, however, is difficult to achieve with conventional home suns, particularly due to the fact that heat radiation may cause skin injury when the human body is too close to the irradiation apparatus.

The heat rays also cause excessive heating of the housing of the apparatus. The housing and the reflector must therefore be made of a heat-resistant material, and especially electrical conduits must be laid at a sufficient distance from the infrared radiation source. As a result, the construction of such devices is bulky. Moreover, infrared radiators arranged in the reflector space reduce the effective reflecting surface and consequently the overall reflector must be made larger in order to achieve the desired tanning effect. Another disadvantage of home suns using IR radiators is the relatively long cooling period required between individual operational periods. Evidently, the above disadvantages are less troublesome in the case of large solaria, but are felt especially when a portable, compact irradiation apparatus is to be designed. The infrared radiators are necessary in prior-art irradiation devices particularly for starting ignition and stabilization of UV gas discharge lamps.

In prior-art irradiation apparatuses, the radiation source is usually mounted in the focal point of a parabolic reflector, so that the reflected rays are transmitted parallel to each other in the direction of the exposed subject. As known, the effect of the reflected radiation is optimum when the rays impinge upon the body of a patient at right angles. Due to the fact however that the human body is not flat, it is necessary to continuously change the direction of incoming rays and the position of the irradiation apparatus. Such continuous adjustments require a correspondingly complicated mechanical design of the apparatus, or an uncomfortable and time-consuming adjustment. Also, the manufacture of parabolic reflectors is relatively difficult and expensive, and the resulting reflectors are bulky and inconvenient for installation in the apparatus housing.

SUMMARY OF THE INVENTION

It is therefore a general object of the present invention to provide a method of and a device for adjustment of intensity of UV radiation from a source which can be readily adapted to individual needs.

An additional object of the invention is to provide such an improved method and device which can individually adjust the strength of radiation not only to humans but also to different photochemical and photobiological processes.

Another object of this invention is to provide an irradiation apparatus of the aforedescribed kind which has low weight, a compact design permitting easy and detachable installation on a household hot-air blower and which is inexpensive to manufacture.

Still another object of this invention is to provide such an improved apparatus which permits a fast, direct pigmentation of a patient's skin by means of longer-wave UVA radiation while only minute portion of undesired heat rays as well as short-wave UVB (causing erythema) and UVC radiation will occur. At the same time, the apparatus should be reliable in operation even during protracted operational periods.

In keeping with these objects and others which will become apparent hereafter one feature of the invention resides in surrounding a conventional source of radiation with a stream of a gas. In doing so, it is of advantage when the gas stream surrounding the source is directed to the object to be irradiated in the direction of UV radiation. It is also advantageous when in the range of the radiation source a dynamic gas pressure is created which is larger than the pressure of the ambient atmosphere. Preferably, the surrounding gas stream is constituted by a gas mixture, such as air. The gas or the gas mixture can be applied to the radiation source either continuously or periodically. It may also be desirable to alternate the surrounding gas stream with an external gas stream and to employ different types of gases. The quantity of the gas as well as the dynamic gas pressure is adjustable according to particular applications. It is also advantageous to use the gases at different temperatures.

In applying a flow of gas into the beam of radiation between the radiation source and the body to be irradiated, especially when the gas stream is directed on the object in the direction of the beam, certain effects are observable which hitherto have not been known. In particular, it has been found that the effect of radiation can be distinctly modified. For example, it has been found that the healing effect of the combined radiation with the gas stream is substantially improved, particularly in skin diseases. If, for example, an air stream surrounds the radiation beam, a substantially faster elimination of psoriasis has been observed; and also other types of skin diseases have been cured in shorter time. The cause of these new effects of the combined radiation and gas stream, is still unknown. Perhaps the composition of the gas mixture is altered by the radiation and/or the irradiated amount of gas supplied per time unit on the object has beneficial results, or the filtering effect of the employed rinsing or surrounding gas improves the quality of the applied radiation in a surprising manner.

An improvement has been achieved already by transmitting a gas stream through the radiation beam in the space between the radiation source and the object to be radiated. The gas stream can be directed perpendicularly to the direction of the radiation beam or inclined thereto at an acute angle.

According to one feature of this invention, the type of gas, the amount of gas, the direction of the gas stream and the gas temperature and the dynamic pressure of the gas are variable. It is advantageous when the gas stream is directed in layers perpendicularly or at an angle to the beam in the space between the radiation source and the object to be irradiated whereby the thickness of the gas layers in the stream the direction of the gas stream, the kind of gas and its temperature are adjustable according to the desired effects.

The modification of the parameters of the applied gas stream can be with advantage combined with prior art adjustment possibilities such as for example the selectively energizable radiation sources and/or filters.

In large area radiators such as used in solaria, the method of this invention can be effectively employed for generating zonal gas streams crossing the radiation beams, particularly in the regions in which the object is to be irradiated at different intensities. The method of this invention is relatively independent from the distance between the source of radiation and the object to be irradiated inasmuch as the intensity of radiation can be modified by the application of a different amount of gas, or by a different thickness of the gas stream layer, or by a different dynamic pressure, or gas temperature in such a manner that the desired intensity of the radiation can be always obtained. This variability of the radiation intensity can be carried out continuously because the aforementioned parameters are also continuously adjustable.

From prior art UV radiators are known especially for irradiating smaller objects, which include in a common housing a source of radiation, and an air nozzle which focusses an air stream on a part of the object which is to be irradiated. The purpose of this air stream is to cool the irradiated areas of the body without effectively interacting with the emitted radiation beam and without surrounding the source of radiation.

In a further modification of this invention, the irradiation apparatus of the aforedescribed kind is constructed as an attachment to a hot-air blower.

In another embodiment, UV irradiation apparatus is devised by means of which the patient's body is exposed to radiation arriving from several directions and with diverging beam so that even curved body surfaces, such as face surfaces for example, can be uniformly exposed.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 is a perspective view of a simple embodiment of the device according to this invention;

FIG. 2 shows a schematic representation of a device for using the method of this invention in large surface solaria;

FIG. 6b is a modified version of the arrangement of FIG. 6a;

DESCRIPTION OF THE PREFERRED EMBODIMENTS

Figure 3:
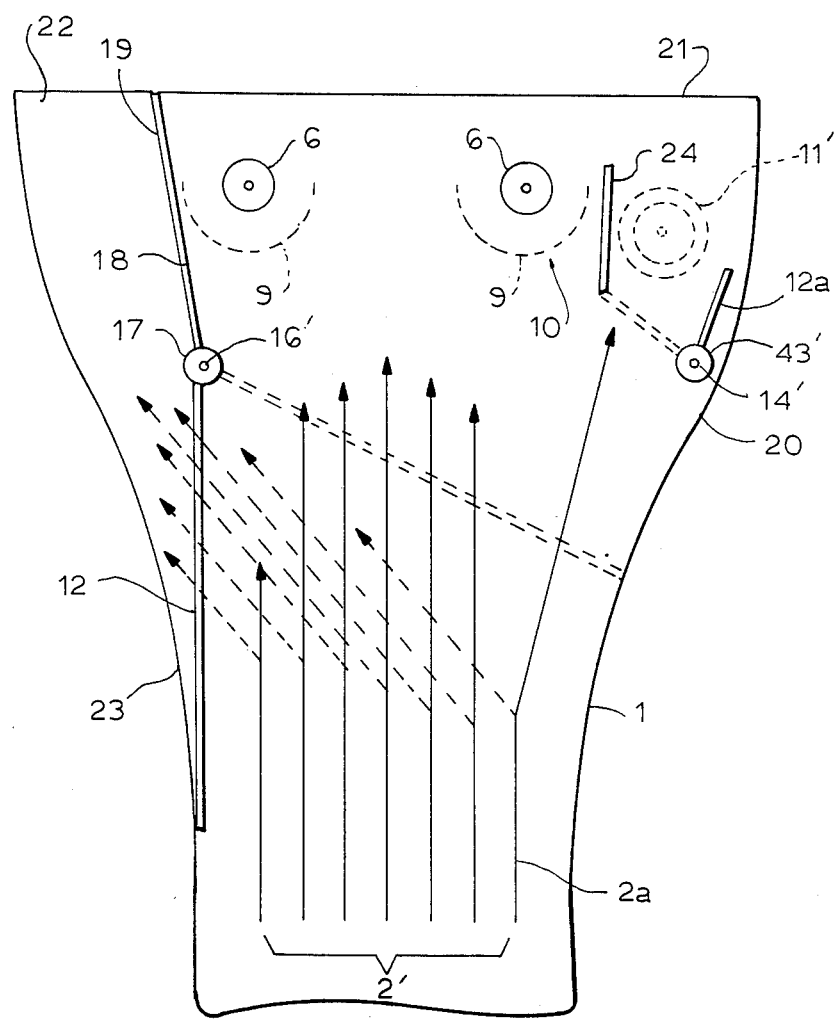
FIG. 3 is a schematic sectional side view of another embodiment of the device of this invention.

The device illustrated in FIG. 1 consists substantially of a gas duct 1 having at its rear end an inlet opening 4 through which a stream of gas 2 is introduced via an attached gas conduit 3. The gas for use in the method of the invention is preferably a gas mixture, such as air, which is supplied from a non-illustrated blower or another source of pressure gas. The temperature of the gas stream, the kind of gas and the amount of gas are adjustable by conventional means. The gas duct 1 also defines an outlet opening 5 in which at least one UV radiation source 6 is exchangeably mounted in an electrical socket 7. The contacts of the socket 7 are connected to power supply wires 8 leading through a lateral wall of the duct 1 or through the rear inlet 4 to be connected to an electrical power source for energizing the source of radiation 6.

In the preferred embodiment of this invention, the radiation source 6 is in the form of an elongated capsule provided at its opposite ends with contact terminals matching the contacts in the socket 7 and is positioned in the outlet opening 5 so as to let the gas stream 2 pass around the radiation beam emanating from the source 6. Preferably, the gas stream 2 is discharged in the direction of the radiation beam to arrive therewith against a non-illustrated object to be irradiated. To facilitate the directional discharge of the gas stream, the gas duct 1 has a configuration of a gas nozzle. The radiation source 6 cooperates with a rear radiation reflector 9 which is formed with holes or perforations 10 through which the gas stream 2 passes around the source 6. If desired, the reflector 9 can be designed with means for varying the size of the perforations 10 or for selectively closing some of these perforations.

In the preferred embodiment of this invention, the open side of the perforated radiation reflector 9 is covered with a baffle plate 11 which is permeable to UV radiation and which increases the dynamic gas pressure around the radiation source 6. Preferably, the baffle plate 11 is of a filtering material passing through certain wavelengths of the UV radiation. The reflector with the baffle plate 11 occupies an intermediate part of the outlet opening 5 so that lateral areas 12 of the outlet opening 5 are free to direct a gas stream 2 against the irradiated object. As mentioned before, the part of the gas stream which passes through the perforations 10 against the inner surface of the baffle plate 11 generates an increased dynamic gas pressure around the radiation source 6. Preferably, the baffle plate 11 is exchangeably attached to the reflector 9 so that plates of different sizes can be readily installed in the duct 1 in order to modify the dynamic pressure of gas in front of the radiator 6. Alternatively, the dynamic pressure can be also adjusted by changing pressure of the gas stream 2 in the duct 1 while using a stationary baffle plate.

Lateral discharge areas 12 in the outlet opening 5 are designed such that the gas stream emanating from the gas duct 1 coincides with radiation beam transmitted by the source 6, whereby the intensity of the radiation beam is changed. If desired, it is also possible to deflect the discharged gas stream from the radiation beam. This deflection can be achieved by means of conventional baffles attached to the gas duct. In some cases it would also be desirable to apply an additional, external gas stream to mix with the circulating gas stream outside from the duct 1. In this manner, a gas cushion or a gas cloud is produced between the radiation source 6 and the object to be irradiated and this gas cushion can be selectively compressed or extended. The external gas stream can be composed of another gas mixture than the gas from the duct 1.

In order to protect the electrical contacts in socket 7, upper and lower metal partitions 13 span the outlet opening 5 in front of these electrical contents. The additional effect of partitions 13 is a further increase of the dynamic gas pressure in the range of the radiator 6. The baffle plate 11 on the other hand protects the source 6 against environment and the user against the source.

The device of this invention as illustrated in FIG. 1 may have dimensions 10×10×5 cm, for example, thus being suitable for irradiation smaller objects or parts of the human body. The flexible gas conduit or hose 3 facilitates manipulation with the device so that the user can reach objects or body areas which are normally accessible with difficulty. The gas source or the gas stream generating apparatus connected to the other end of the flexible hose 3 is stationary.

FIG. 2 illustrates another embodiment of the device according to this invention, including a composite radiator 15 suitable for use in solaria, for example. The radiator 15 is assembled of an array of radiation sources 6 each equipped with a radiation reflector 9 formed with a plurality of holes or perforations 10. The gas ducts 1 surrounding the radiation sources and the reflectors are connected with their inlet openings to a common gas supply conduit 16 connected with the source of a gas stream 2. The outlets of the gas duct 1 are arranged in a single plane directed against an object to be irradiated. The radiation beams 18 from individual sources 6 are directed parallel to each other and so are the gas streams 17 surrounding the radiation sources 6 and the transmitted beams. Similarly, as in the preceding example, the perforations 10 in respective reflectors 9 can be adjustable. Also, the inlet parts of gas ducts 1 are with advantage provided with control valves so that the gas supply to individual radiation sources can be selectively switched on or off. In this manner, the large area radiator 16 of the device 14 of this invention is suitable for adjusting zones of different radiation intensity.

The method of this invention thus modifies and improves by simple means the effects of UV radiation, so that radiation therapy is substantially more compatible with human skin, causes faster healing of infected areas of the skin and also causes faster effects in chemical and biological processes. This improvement in the effects of radiation is explained by the action of the gas cushion surrounding the source of radiation and by the fact that the gas stream present between the source and the object to be irradiated has a different composition with respect to the ambient atmosphere. The difference results from the generation of ozone and also due to the increased dynamic gas pressure and to intensive circulation of the gas around the radiation source.

According to the embodiment of FIG. 3, it is possible not only to change the direction of the discharged air stream but also to admix to the air stream additional gas or vapors which influence the exposure of human skin, particularly in order to make the irradiation more bearable. In this embodiment, two radiation sources 6, each with a perforated reflector 9, are arranged side-by-side in the housing of air duct 1. In a marginal part of the outlet of the duct, there is provided a container 11' having gas- or vapor-permeable walls, so that air stream 2 can pass therethrough and entrain gaseous components from an evaporative substance which is present in the container 11'. Preferably, this substance is first placed in an exchangeable gas-permeable capsule which is inserted in the container 11'. As indicated in full arrows, in one operative position the air stream 2 flows past the radiators 6 and a partial stream 2a flows through the container 11' where it is loaded with additional substances such as perfume, an aromatic oil, or the like, and is redirected to the treated subject. The adjoining air stream 2 passes through the reflectors 9 and circulates about the radiation sources 6. Consequently, there results a combined effect of UV radiation with irradiated air stream and the auxiliary perfume-air mixture.

In order to increase the versatility of the apparatus, the air stream 2 can be deflected so as to bypass the radiators and the auxiliary evaporative substance. For this purpose, a tiltable wall or partition 12' is mounted on a rotary axle 16 located in the expanded part of the duct 1 and passing through its wall. The projecting part of axle 16' is connected to a control knob 17. The tiltable wall 12 is adjusted in shape to the cross section of duct 1. In one operative position, indicated by full lines, the wall 12' extends parallel to the reduced lower part of duct 1 and permits unobstructed passage of the air stream 2 toward the radiators 6 and the auxiliary container 11'. In a blocking position, indicated by dashed lines, the tiltable wall is rotated across the channel 1 and the air stream bypasses the radiator 6 and the evaporative substances in container 11, thus eliminating the function of the latter.

Preferably, an additional partition 12a is pivotably mounted about an axle 14 in the range of the container 11'. In this embodiment, the partition 12a is substantially shorter than the partition 12', and its function is to divert the air stream 2 from reaching the container 11' for evaporative substances. Preferably, the fixed partition 24 is mounted between the container 11 and the adjoining radiator 6, and the additional partition 12a is tiltable against the lower ends of the fixed partition 24 as indicated by dashed lines. The axle 14' of the additional partition 12a also passes through the walls of the duct 1 and is connected to a control knob 13.

A similar fixed partition 18 is provided at the opposite side of the duct 1 above the axle 16' to define a bypass channel 22 through which the air stream is directed when the main partition 12' blocks the passage of the air stream to the radiators. If desired, the fixed partition 18 is inclined at an angle at which the diverted air stream is directed away from the irradiated subject.

Figure 4:
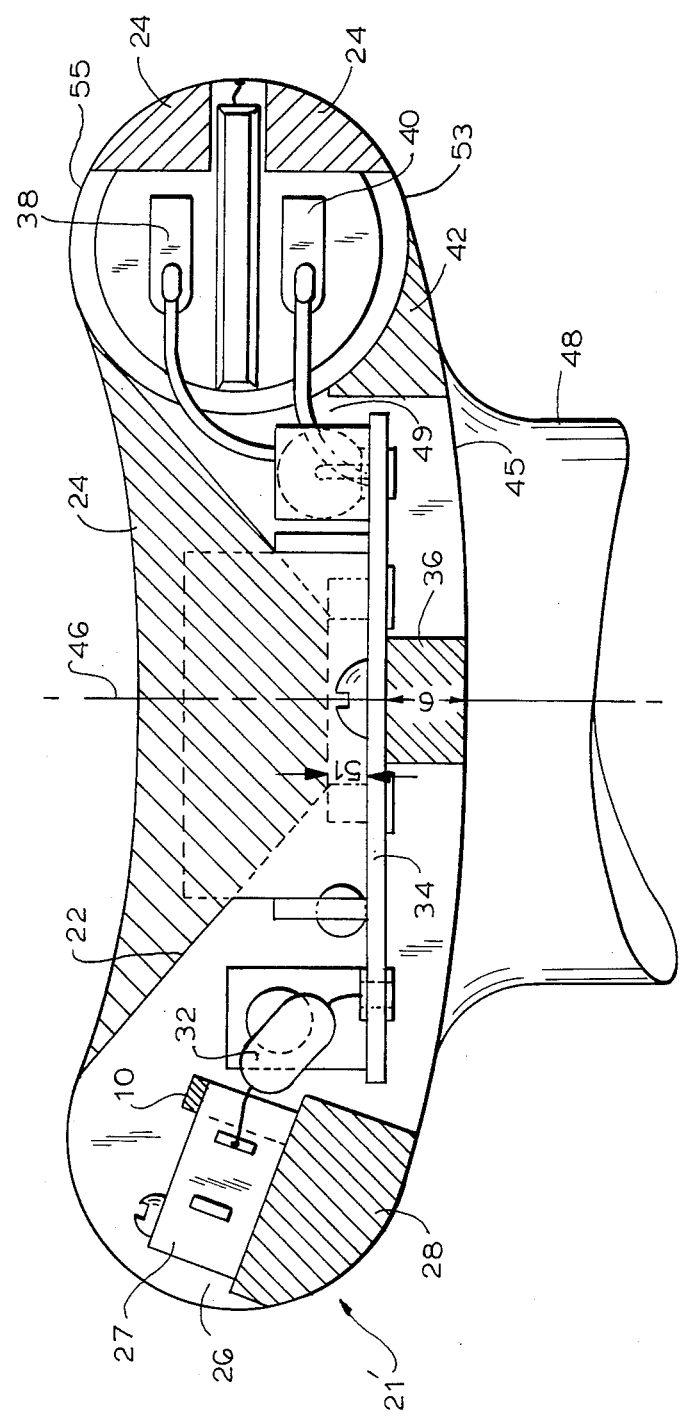
FIG. 4 is a schematic sectional side view of still another embodiment of an irradiation device of this invention.
Figure 5:
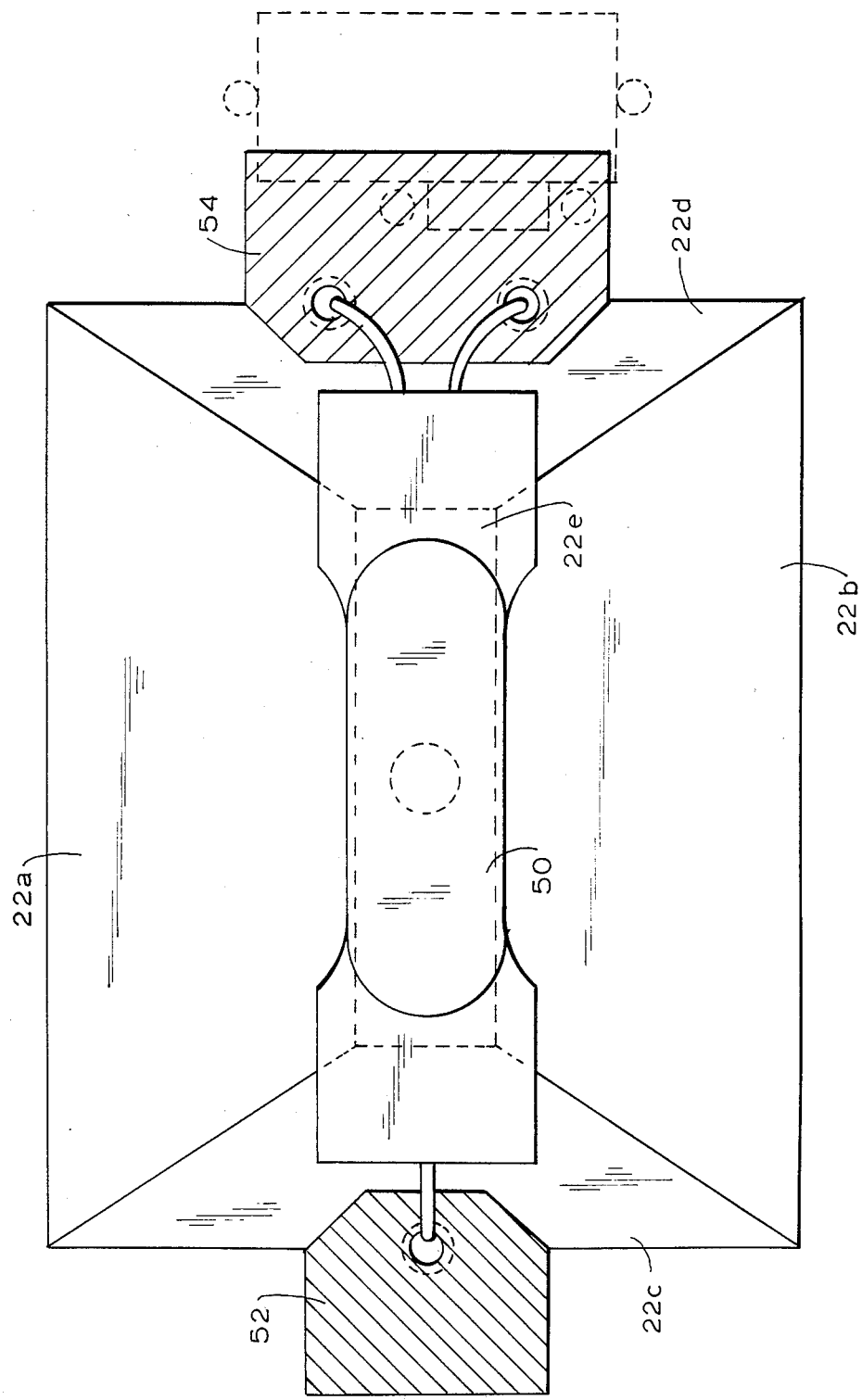
FIG. 5 is a plan view of the device of FIG. 4.

In another embodiment of the irradiation apparatus as disclosed in FIGS. 4 and 5, housing 21 has an extended front part defining concave front and rear walls when viewed from the side of irradiation and having rounded or semicircular ends. The radius of curvature of the rear wall is for example 139 nm whereas the radius of curvature of the front concave wall is about 114 mm.

The concave front wall is formed with a rectangular opening accommodating a compound reflector (FIG. 5) assembled of five reflecting surfaces 22a–22e. A non-illustrated UV-lamp is mounted in the bottom part of reflecting space 24.

The rounded or semicircular ends of housing 24 contain a pressure knob 26 leading to a microswitch 7" which is mounted on an insulating mount 28 and secured against rotation by a pin 30. A thermal switch 32 connects the main switch 27 to a conductive plate 34 extending below the reflector 22 and being supported on a central mount 36. The conductive plate 34 supports a socket and power supply conductor for the UV lamp. The electrical circuit for the lamp includes two capacitors 38 and 40 which are arranged in a holder 42 at the opposite rounded end of the housing 21 and are protected against torsional or axial displacement by an antitorsion shield 44. Preferably, the holder is resiliently mounted.

The bottom surface of the conductive plate 34 is spaced apart from the rear wall 45 about a distance of about 6 mm. The distance 51 between the upper surface of the conductive plate 34 and the bottom of the reflector 22 amounts to about 3 mm. In designing the upper part of housing 21, the necessary tolerances of the UV lamp must be taken into account. The upper housing part is provided with two cut-outs permitting the access to soldering points of the connection wires to the UV lamp. These cut-outs are covered by the lamp mount and by additional end caps.

The rear wall 45 communicates with an extension of slip-on duct 48 which is integrally connected to the upper housing part 21. The slip-on duct 48 is dimensioned such as to be insertable on the discharge tube of a hot air blower. The connection is secured by means of a clamping seat or also by means of threads or by fastening screws.

The duct 48 communicates with the interior of the upper housing part 21 through air passages 49 around the edges of the conductive plate 34, through which the air can flow past the capacitors 38 and 40 and is discharged through openings 53 and 55 at the outer edges of the upper housing part 21.

FIG. 5 shows in a top view of the apparatus of FIG. 4 the UV lamp 50 mounted at the bottom of the assembled reflecting pieces 22a through 22e inclined so as to reflect light on the subject to be irradiated. The UV lamp 50 is connected to two mounting sectors 52 and 54. The lamp is provided with a short-circuit protection device in the form of a mercury switch for example.

The following table lists by way of example operational parameters of the radiation apparatus according to this embodiment:

TABLE I

| Wavelength range | Wavelength λ [nm] | Radiation Flux $\phi_e$ [W] | Radiation Intensity E' at a distance of 1 m [μW/cm²] | Distribution of E' [%] |
|---|---|---|---|---|
| UV-C | 248.2 | 0.82 | 7.585 | 2.8 |
|  | 252.0–257.6 | 2.43 | 22.478 | 8.2 |
|  | 264.0–265.2 | 1.49 | 13.783 | 5.0 |
|  | 269.9 | 0.24 | 2.220 | 0.8 |
|  | 275.2–276 | 0.20 | 1.850 | 0.7 |
| UV-B | 280.4 | 0.56 | 5.180 | 1.9 |
|  | 289.4 | 0.30 | 2.775 | 1.0 |
|  | 292.5 | 0.06 | 0.555 | 0.2 |
|  | 296.7 | 0.86 | 7.955 | 2.9 |
|  | 302.2 | 1.59 | 14.707 | 5.4 |
|  | 313.3 | 3.47 | 32.098 | 11.7 |
| UV-A | 334.1 | 0.36 | 3.330 | 1.2 |
|  | 365.0–366.3 | 5.36 | 49.580 | 18.0 |
|  | 390.6 | 0.04 | 0.370 | 0.1 |
|  | 404.7–407.8 | 2.00 | 18.300 | 6.8 |
|  | 435.8 | 3.06 | 28.305 | 10.3 |
|  | 491.6 | 0.06 | 0.555 | 0.2 |
|  | 546.6 | 3.64 | 33.670 | 12.3 |
|  | 577.0–579.0 | 3.12 | 28.860 | 10.5 |
|  | Σ | 29.66 | 274.36 | 100.0 |

Figure 6A:
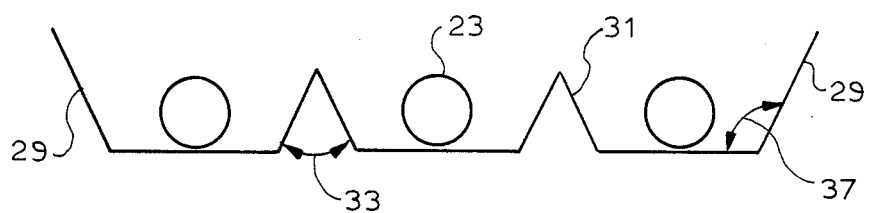
FIG. 6a shows schematically an arrangement of UV radiators having reflectors.
Figure 6B:
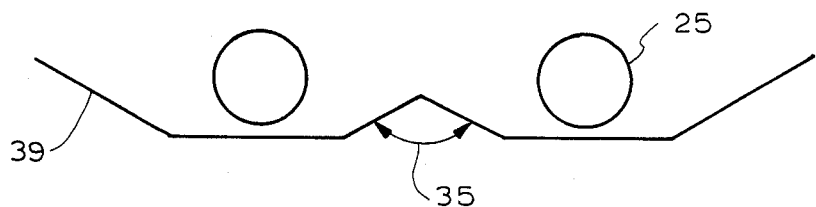
Figure 6C:
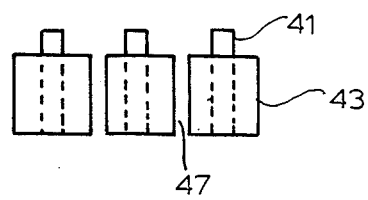
FIG. 6c shows schematically an arrangement of corresponding sockets.

FIGS. 6a and 6b illustrate effectively different reflector arrangements for use with several radiation sources 23 or 25. The reflecting lateral mirror surfaces 29 or 39 are longer than the adjoining intermediate mirror surfaces 31. Angles of inclination 33, 35 and 37 are adjustable to produce different diverging radiation beams. Also, the radiators 23 and 25 in each arrangement can be of the same type or can differ from each other.

Pistons 41 with sockets 43, schematically illustrated in FIG. 6b, are spaced apart from each other in order to obtain a good cooling effect through the gas 47.

Figure 7:
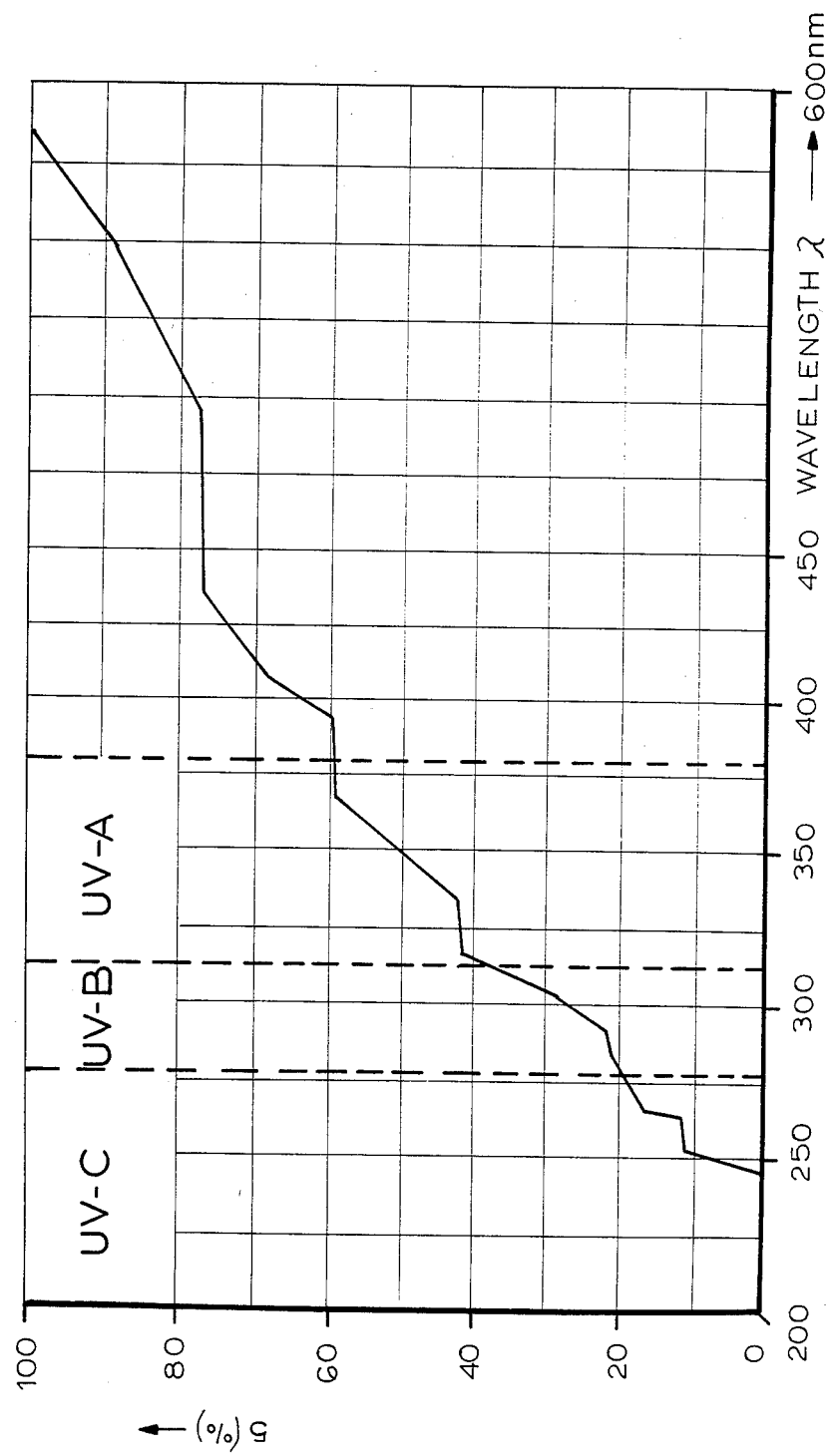
FIG. 7 is a plot diagram of the spectral distribution of a high-pressure mercury-vapor lamp.

FIG. 7 shows graphically the relationship of summation frequency S of the radiation intensity E' (Table I) measured at a nominal value versus radiation wavelength.

Figure 8:
FIG. 8 is a plot-diagram of the spectral distribution of FIG. 7 after reflection on different reflectors.

FIG. 8 shows in a plot diagram a spectral distribution S of radiation emitted against a subject for various upper surface layers on the reflector 22, of which:

Curve #2 is a gold-coated superrefined steel layer (lossy).
Curve #2 is matte aluminum (sand-blasted).
Curve #3 is eloxidized yellow aluminum
Curve #4 is eloxidized blue aluminum.
Curve #5 is eloxidized purple aluminum.
Curve #6 is glossy, superrefined steel (chromium).

From the diagram it is evident that curves pertaining to surface layers #3 (eloxidized yellow aluminum) and #6 (glossy, superrefined steel) (chromium) exhibit the most advantageous qualities.

Figure 9:
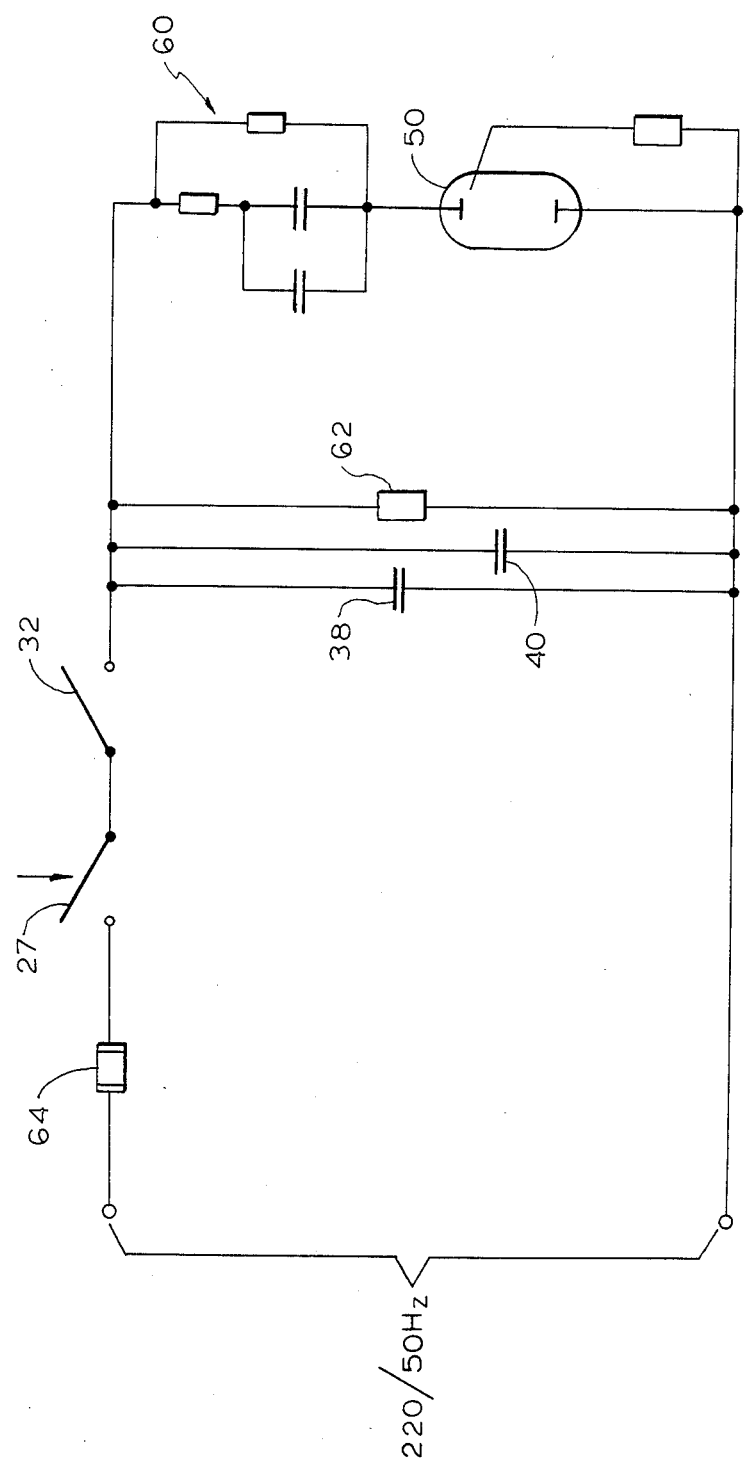
FIG. 9 is a circuit diagram of an ultraviolet (UV) lamp.

FIG. 9 shows a circuit diagram of a UV lamp 50. The lamp is connected in series with a load network 60 composed of parallel connection of resistors and capacitors and via switches 32 and 27 and a protective fuse 64 to an alternating main voltage. Capacitors 38 and 40 are connected parallel to a discharge resistor 62 connecting the live conductor to the ground conductor. If using for example a mercury vapor high-pressure lamp OS 125 (manufacturer Osram GmbH, Berlin or Munich) as the UV lamp 50, there is employed a discharging resistor of 0.3 megohms and capacitor 38 has a value between 0.4 and 0.5 microfarads. The thermal switch 32 is activated at about 80° C. to interrupt the power supply.

The entire irradiation apparatus of FIGS. 4–9 weighs only between 250 and 300 grams and is of a size slightly exceeding a cigarette box. Due to this small size, it can be carried with ease.

The mercury vapor radiator has a nominal power of 125 W. The prescribed electrode voltage for the lamps is 85 volts ±11 volts at a nominal current of 2 A. For operation at the main current the lamps need a series resistor of 74 ohms. In this instance, the required resistance is achieved by a series connection of a capacitor of about 30 microfarads. The ignition voltage of the electrodes of the lamp is 180 volts. After the ignition, the lamps behave as an ohmic resistor. With increasing temperature of the piston the lamp approaches its saturation current ($I_{sat}$) at which all load carriers are sucked off. As a consequence, with increasing voltage, no current increase will occur. The radiator operates in the non-linear part of its characteristic line and shapes the momentary value of its voltage.

The impedance of the series-connected capacitor becomes low at higher frequencies, and the radiator is supplied with a voltage which exceeds the prescribed ignition voltage and the whole apparatus is turned off.

Since the maximum saturation current and this the charge carriers is directly proportional to the operational temperature of the radiator, it is possible to control the power as well as the wavelength, and thus the kind of transmitted radiation to a limit value by cooling the radiator.

Figure 10:
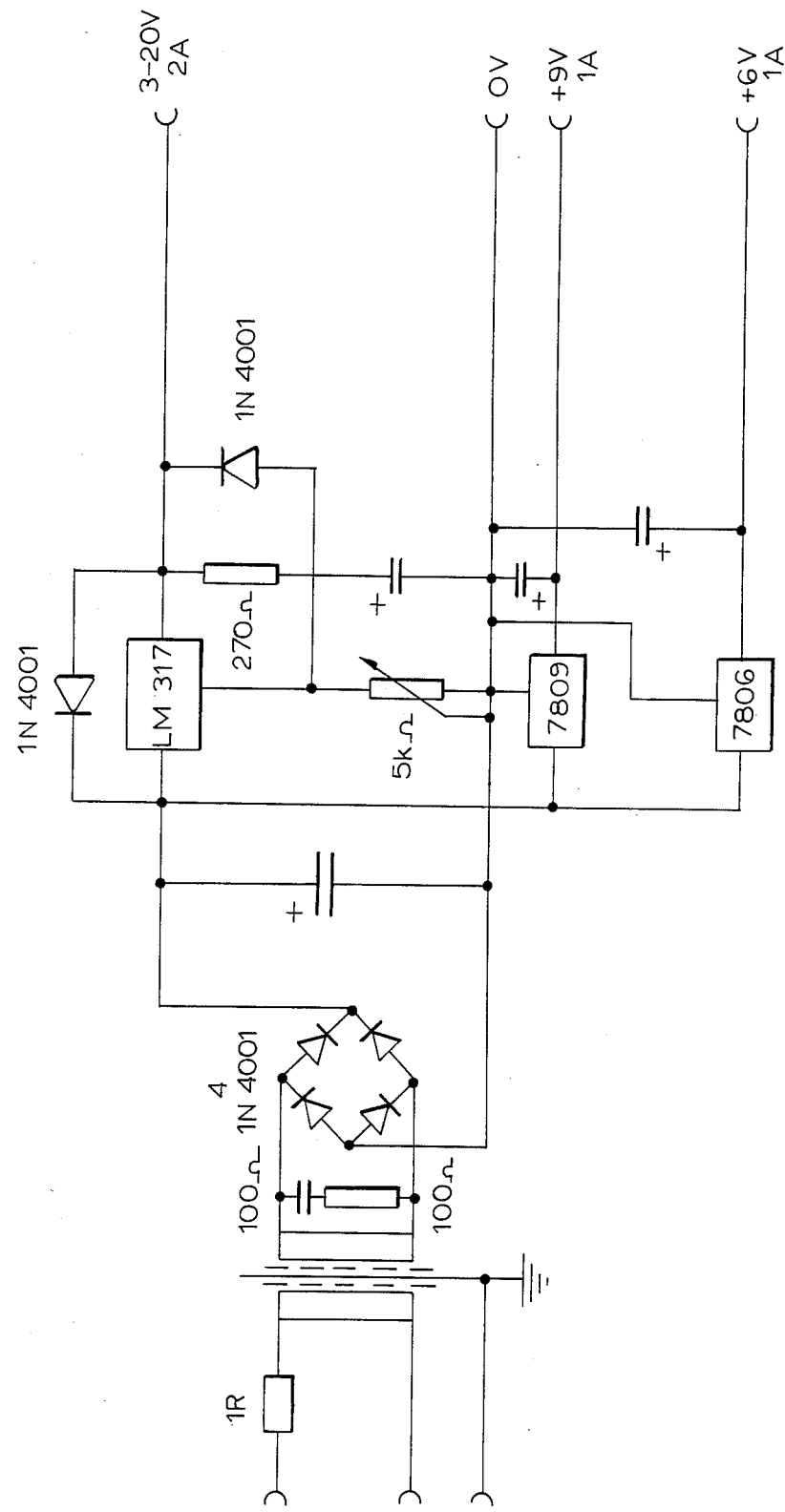
FIGS. 10 and 11 are circuit diagrams of a power supply and an indication module, respectively.
Figure 11:
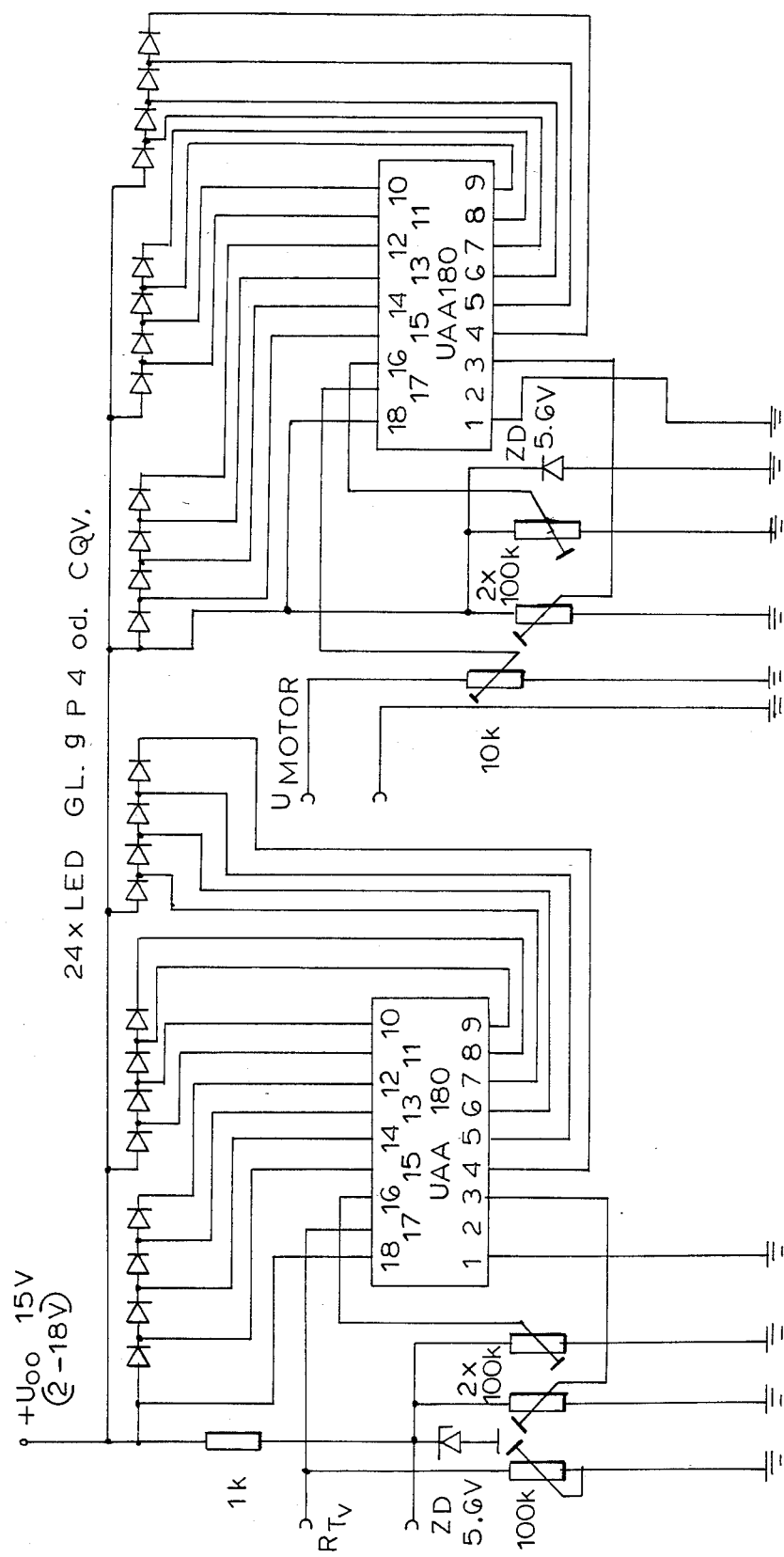

FIGS. 10 and 11 show a circuit diagram of a warning and switching device for use in connection with the irradiation apparatus and the motor of an air blower of this invention. FIG. 10 illustrates a power supply circuit including four rectifying diodes (IN4001) and a voltage regulating circuit assembled of intergrated modules LM317, 7809 and 7806. The rectified output voltage is applied to the indicating or warning and switching circuit shown in FIG. 11. The warning circuit includes a first integrated subcircuit UAA 180 with its input connected to terminals $R_T$ of an irradiation (dose) sensing device. A second integrated subcircuit UAA 180 has its input connected to terminals V motor of an air blower for detecting voltage applied to the motor of the air blower. The outputs of both subcircuits UAA 180 are connected to two series of light emitting diodes GL 9 P4 arranged respectively as an indicating bars. Depending on the number of activated diodes in the first bar, a warning signal is generated to indicate that a predetermined dose of radiation has been received by the user. The second bar of diodes is indicative of the performance of the air blower.

It will be understood that each of the elements described above or two or more together may also find a useful application in other types of constructions differing from the types described above.

While the invention has been illustrated and described as embodied in a specific example of a UV radiator, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the following claims.

I claim:

1. A portable irradiation apparatus, particularly for therapeutic and cosmetic purposes, comprising a box-shaped housing having a major wall formed with an outlet opening and an opposite major wall formed with an inlet opening, a reflector mounted in said outlet opening, a circuit board attached to said housing between the bottom of said reflector and said inlet opening for supporting a UV-lamp and power supply circuit for the UV-lamp, the power supply circuit including at least one capacitor, and a slip on air duct means communicating with the inlet of the housing and being attachable to an air blower to introduce a circulating stream of cooling gas past the UV-lamp and the electrical components inclusive of said capacitor.

2. An apparatus as defined in claim 1, wherein the slip on air duct means is a tubular piece integrally connected to the housing around the inlet opening.

3. An apparatus as defined in claim 2, comprising air passages between the circuit board and the walls of the housing and air discharge openings adjoining the rim of said reflector.

4. An apparatus as defined in claim 3, wherein the reflector is assembled of a plurality of flat surfaces.

5. An apparatus as defined in claim 4, wherein said reflector is assembled of five flat surfaces.

6. An apparatus as defined in claim 4, wherein the reflecting surfaces are inclined at such an angle to the UV-lamp as to reflect a diverging radiation beam.

7. An apparatus as defined in claim 1, wherein the reflector is made of a synthetic material.

8. An apparatus as defined in claim 1, wherein the reflecting surface of the reflector is a metal layer applied galvanically or deposited by evaporation of a metal.

9. An apparatus as defined in claim 8, wherein the reflecting surface is made of superrefined steel.

10. An apparatus as defined in claim 8, wherein said reflecting surface is of eloxidized yellow aluminum.

11. An apparatus as defined in claim 8, wherein said reflecting surface is made of a layer of material reflecting with preference UV-A radiation.

12. An apparatus as defined in claim 1, wherein said UV-lamp is a high-pressure mercury vapor lamp emitting a high percentage of long-wave UV-A rays.

13. An apparatus as defined in claim 12, wherein the entire spectrum of the emitted radiation is substantially in the wavelength range between 240 nm and about 585 nm.

14. An apparatus as defined in claim 1 comprising filtering means for suppressing short-wave UV-B and UV-C radiations.

15. An apparatus as defined in claim 1 comprising filtering means for suppressing long-wave visible light and IR radiation.

16. An apparatus as defined in claim 1 wherein said capacitor is connected parallel to said UV-lamp.

17. An apparatus as defined in claim 16 further including a discharge resistor connected parallel to said capacitor.

18. An apparatus as defined in claim 16 comprising on plurality of parallel connected capacitors arranged in said stream of cooling gas from the air blower.

19. An apparatus as defined in claim 1 wherein said power supply circuit includes as temperature sensitive protection switch for the UV-lamp.

20. An apparatus as defined in claim 1 wherein said power supply circuit includes an electronically controlled timing switch.

21. An apparatus as defined in claim 1 further comprising an circuit for generating a warning signal and/or for disconnecting the UV-lamp when a predetermined irradiation dosis has been obtained.

22. An apparatus as defined in claim 1 comprising a short-circuit responsive protection switch for the UV-lamp.

23. An apparatus as defined in claim 22 wherein said short-circuit responsive protection switch is a mercury switch.

* * * * *